United States Patent
Saito (10) Patent No.: US 12,318,519 B2
(45) Date of Patent: Jun. 3, 2025

(54) OXYGENATOR WITH PRESSURE RELIEF AND SAMPLING

(71) Applicant: Terumo Kabushiki Kaisha, Tokyo (JP)

(72) Inventor: Takashi Saito, Kanagawa (JP)

(73) Assignee: Terumo Kabushiki Kaisha, Tokyo (JP)

( * ) Notice: Subject to any disclaimer, the term of this patent is extended or adjusted under 35 U.S.C. 154(b) by 612 days.

(21) Appl. No.: 17/679,283

(22) Filed: Feb. 24, 2022

(65) Prior Publication Data

US 2022/0176024 A1 Jun. 9, 2022

Related U.S. Application Data

(63) Continuation of application No. PCT/JP2020/033712, filed on Sep. 7, 2020.

(30) Foreign Application Priority Data

Sep. 17, 2019 (JP) ................................. 2019-167953

(51) Int. Cl.
*A61M 1/16* (2006.01)
*A61M 1/36* (2006.01)
*B01D 63/02* (2006.01)

(52) U.S. Cl.
CPC ........ *A61M 1/1625* (2014.02); *A61M 1/1698* (2013.01); *A61M 1/3623* (2022.05);
(Continued)

(58) Field of Classification Search
None
See application file for complete search history.

(56) References Cited

U.S. PATENT DOCUMENTS 5,162,101 A * 11/1992 Cosentino ............. F28F 21/062
422/46
10,188,780 B2  1/2019 Wu et al.
(Continued)

FOREIGN PATENT DOCUMENTS

JP   2006122111 A   5/2006
JP   2016019666 A   2/2016
(Continued)

OTHER PUBLICATIONS

Written Opinion of the International Searching Authority, PCT/JP2020/033712, Oct. 27, 2020.
(Continued)

*Primary Examiner* — Susan S Su
*Assistant Examiner* — Katherine-Ph Minh Pham
(74) *Attorney, Agent, or Firm* — MacMillan, Sobanski & Todd LLC (57) ABSTRACT

A cover member (36) that forms an end of a housing (26) of an oxygenator (10) has a recessed wall portion (88) recessed relative to a cover main body (74) further toward a side of a gas exchange unit (30) than an inner surface (74a). A pressure control hole (86) is formed through a main body (74) of the cover member (36), and a sampling port (90a) is disposed in the second recessed wall portion (88) to collect gas guided out from the gas exchange unit (30). The sampling port (90a) faces, at its inner opening portion (92), a second outlet side end face (31b) of the gas exchange unit (30).

9 Claims, 6 Drawing Sheets

(52) U.S. Cl.
CPC .... *B01D 63/031* (2022.08); *B01D 2313/2011* (2022.08); *B01D 2313/24* (2013.01)

(56) References Cited

U.S. PATENT DOCUMENTS

2007/0166190 A1\* 7/2007 Ogihara .............. A61M 1/3627
422/45
2017/0348639 A1\* 12/2017 Mizoguchi .......... A61M 1/1623

FOREIGN PATENT DOCUMENTS

| WO | 2016009780 A1 | 1/2016 |
| WO | 2018026671 A1 | 2/2018 |

OTHER PUBLICATIONS

International Search Report, PCT/JP2020/033712, Oct. 12, 2020.
Extended European Search Report 20865341.0, Sep. 5, 2022.

\* cited by examiner

OXYGENATOR WITH PRESSURE RELIEF AND SAMPLING

CROSS REFERENCE TO RELATED APPLICATIONS

This application is a continuation of PCT Application No. PCT/JP2020/033712, filed Sep. 7, 2020, based on and claiming priority to Japanese Application No. 2019-167953, filed Sep. 17, 2019, both of which are incorporated herein by reference in their entirety.

BACKGROUND OF THE INVENTION

The present invention relates to an oxygenator.

An oxygenator including a gas exchange unit, which has hollow fiber membranes allowing blood to undergo gas exchange, and a housing with the gas exchange unit accommodated therein is disclosed, for example, in PCT Patent Publication No. WO2016/009780. The housing has a housing main body, a first cover member disposed on one end portion of the housing main body such that the gas exchange unit is covered at an inlet side end face thereof where gas inlets of the hollow fiber membranes are located, and a second cover member disposed on the other end portion of the housing main body such that the gas exchange unit is covered at an outlet side end face thereof where gas outlets of the hollow fiber membranes are located. The first cover member is provided with a gas introduction port for guiding gas into the housing, and the second cover member is provided with a gas exit port for guiding the gas which has flowed through the gas exchange unit to an outside of the housing.

In the oxygenator as mentioned above, a sampling port for collecting the gas guided out from the gas exchange unit may be disposed in the second cover member to enable a concentration of the gas to be measured. Through the second cover member, however, a pressure control hole is also formed to control (e.g., restrict) a pressure of the gas guided out from the gas exchange unit. There is hence a potential problem that ambient air flowing into the housing from the pressure control hole may enter and mix into the sampling port so that the composition of the gas collected from the sampling port may change.

SUMMARY OF THE INVENTION

With such a problem in view, the present invention has as an object thereof the provision of an oxygenator capable of efficiently guiding gas which has been guided out from a gas exchange unit into a sampling port while entry and subsequent mixing of ambient air into the sampling port is suppressed.

In an aspect of the present invention, there is provided an oxygenator including (1) a gas exchange unit having hollow fiber membranes that allow blood to undergo a gas exchange extending between first and second longitudinal ends and being configured to allow blood to undergo gas exchange, wherein the first longitudinal end comprises an inlet side end face thereof where gas inlets of the hollow fiber membranes are located, and wherein the second longitudinal end comprises an outlet side end face thereof where gas outlets of the hollow fiber membranes are located and (2) a housing provided with a gas inflow port and a gas outflow port. The housing includes a housing main body with the gas exchange unit accommodated therein, a first cover member disposed on one end portion of the housing main body enclosing the first longitudinal end of the gas exchange unit, and a second cover member disposed on the other end portion of the housing main body enclosing the second longitudinal end of the gas exchange unit. The second cover member has a cover main body facing the outlet side end face of the gas exchange unit, and a recessed wall portion which is recessed relative to the cover main body to be closer to the outlet side end face of the gas exchange unit than an inner surface of the cover main body. A pressure control hole is formed through the cover main body to control a pressure of gas guided out from the gas exchange unit. A sampling port is disposed in the cover main body to collect a respective portion of the gas guided out from the gas exchange unit. The sampling port faces, at an inner opening portion thereof, the outlet side end face of the gas exchange unit.

In another aspect of the present invention, an oxygenator for treating an extracorporeal blood flow comprises a cylindrical housing with a first cover member at a first end defining a gas inlet and a second cover member at a second end defining a gas outlet and a sampling port, and a gas exchange unit comprised of cylindrically-wound hollow fiber membranes each extending from an annular inlet side end face proximate the first cover member to an annular outlet side end face proximate the second cover member. The second cover member has a main wall portion spaced from the outlet side end face of the gas exchange unit by a first distance and a recessed wall portion spaced from the outlet side end face of the gas exchange unit by a second distance which is less than the first distance. The main wall portion includes a pressure control hole configured to provide pressure relief within the housing. The sampling port is disposed on the recessed wall portion so that a spacing of an inner end of the sampling port from the outlet side end face is less than a spacing of the pressure control hole from the outlet side end face, whereby a gas flowing from the gas exchange unit flows to the sampling port more efficiently than an ambient air flowing through the pressure control hole. Additionally, the sampling port may be spaced by 60° or greater in a peripheral direction of the second cover member relative to the pressure control hole.

According to the present invention, the pressure control hole is formed in the cover main body, and the sampling port is disposed in the recessed wall portion recessed further toward the side of the gas exchange unit than then inner surface of the cover main body. Owing to this configuration, ambient air flowed from the pressure control hole into the housing can be suppressed from entering and mixing into the sampling port compared with a case in which the sampling port is disposed in the cover main body. In addition, the inner opening portion of the sampling port faces the outlet side end face of the gas exchange unit, so that the gas guided out from the outlet side end face of the gas exchange unit can be efficiently guided into the sampling port.

DETAILED DESCRIPTION OF PREFERRED EMBODIMENTS

Hereinafter, a preferred embodiment of an oxygenator according to the present invention will be exemplified and described with reference to the accompanying drawings.

Figure 1:
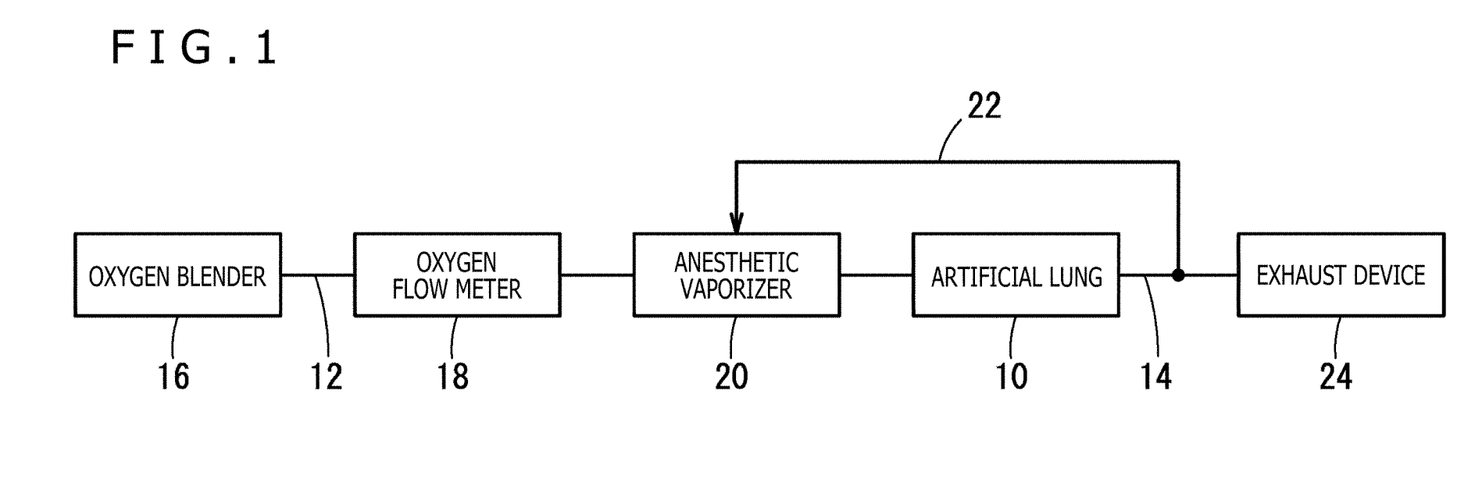
FIG. 1 is an explanatory block diagram illustrating a flow of gas to be supplied to an oxygenator according to an embodiment of the present invention.

An oxygenator 10 illustrated in FIG. 1 is a medical device that temporarily replaces a function of lungs in a surgery such as a cardiac surgery on a human body. In other words, the oxygenator 10 is a device that performs control of a blood temperature and control of a blood oxygen concentration in extracorporeal blood circulation. The oxygenator 10 according to this embodiment may also supply an anesthetic to blood in extracorporeal blood circulation.

In FIG. 1, connected to the oxygenator 10 are a gas supply line 12 for supplying gas (oxygen gas and anesthetic gas) to the oxygenator 10, and a gas discharge line 14 to which gas (e.g., carbon dioxide gas removed from blood, any remaining oxygen gas, or any remaining anesthetic gas) discharged from the oxygenator 10 is guided. In the gas supply line 12, an oxygen blender 16, an oxygen flow meter 18, and an anesthetic vaporizer 20 are sequentially arranged from an upstream portion to a downward portion.

The oxygen blender 16 serves to control a concentration of oxygen by blending compressed air and compressed oxygen together. The oxygen flow meter 18 measures a flow rate of oxygen in gas supplied from the oxygen blender 16. The anesthetic vaporizer 20 mixes anesthetic gas which has been vaporized from an anesthetic into oxygen gas. In the oxygenator 10, carbon dioxide gas in the blood removed from a patient is eliminated, and the oxygen gas and the anesthetic gas are supplied into the blood.

To the gas discharge line 14, a circulation line 22 is connected to guide a portion of the anesthetic gas which has been discharged from the oxygenator 10, to the anesthetic vaporizer 20. On a downstream side of a point of connection with the circulation line 22 in the gas discharge line 14, an exhaust device 24 is arranged to discharge any surplus anesthetic gas to an outside space (for example, outside an operating room or the like).

Figure 2:
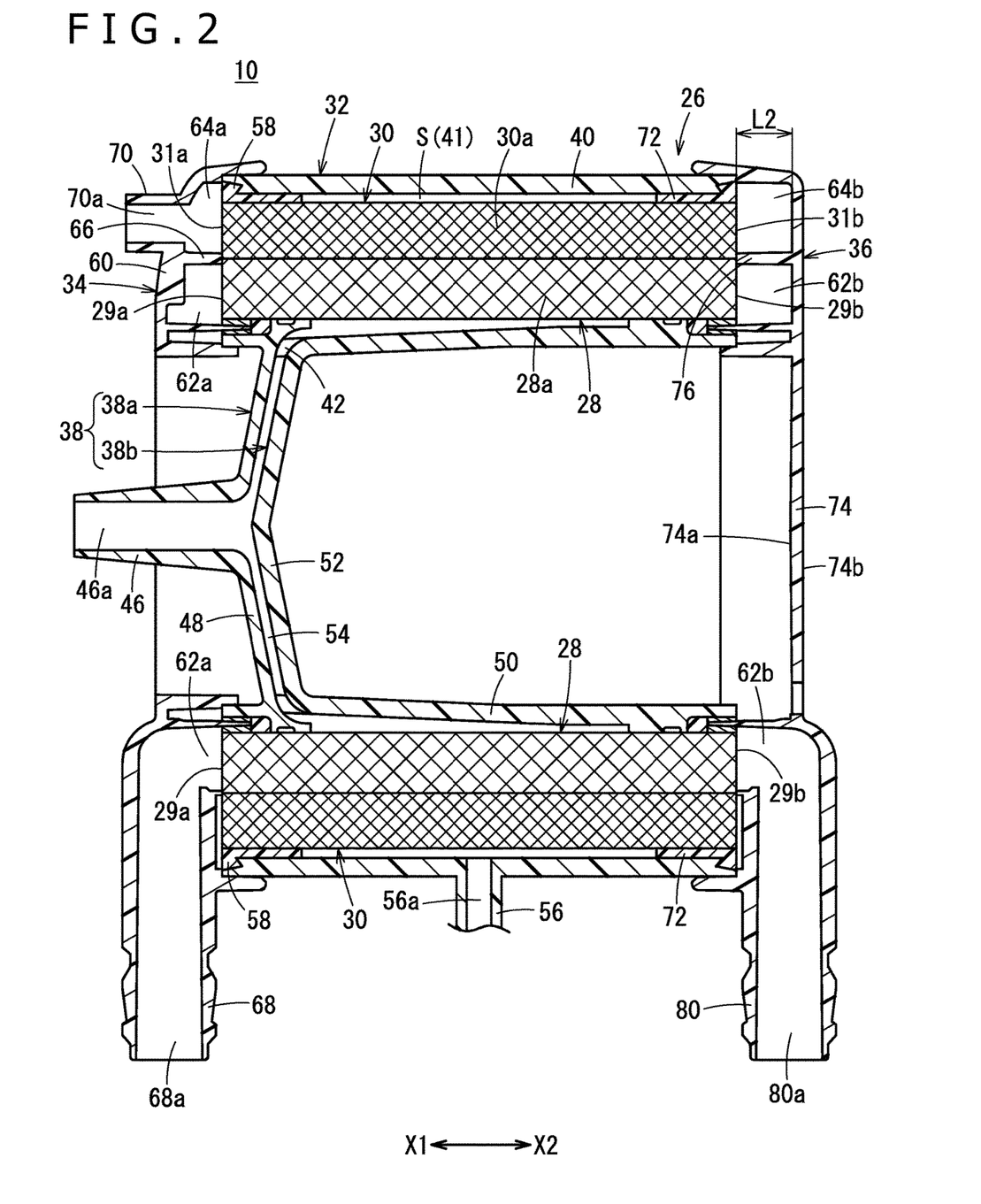
FIG. 2 is a vertical cross-sectional view of the oxygenator of FIG. 1.

As depicted in FIG. 2, the oxygenator 10 includes a housing 26, a heat exchange unit 28, and a gas exchange unit 30. The housing 26 is formed of a hard resin. The housing 26 has a housing main body 32 with the heat exchange unit 28 and the gas exchange unit 30 accommodated therein, a first cover member 34 disposed on one end portion (an end portion in a direction of an arrow X1) of the housing main body 32, and a second cover member 36 disposed on the other end portion (an end portion in a direction of an arrow X2) of the housing main body 32.

The housing main body 32 includes a core 38 forming a central part of the oxygenator 10, and an outer cylinder 40 disposed on an outer peripheral side of the core 38. Between the core 38 and the outer cylinder 40, an annular accommodation space S is formed to accommodate the cylindrical heat exchange unit 28 and the cylindrical gas exchange unit 30. The accommodation space S functions as a blood flow path 41.

The core 38 includes a first core section 38*a* forming one end portion of the core 38 and a second core section 38*b* forming a portion that includes the other end portion of the core 38. The first core section 38*a* and the second core section 38*b* are connected to each other by a plurality of connection portions 42.

The first core section 38*a* has a tubular blood inflow portion 46, and an annular wall portion 48 extending outward in a radial direction from the blood inflow portion 46. The blood inflow portion 46 forms a blood inflow port 46*a* into which the blood guided from the patient via an undepicted blood removal line flows.

The second core section 38*b* is formed in a bottomed cylindrical shape, and has a cylinder portion 50, and a closing portion 52 disposed at one end portion of the cylinder portion 50. The closing portion 52 is arranged to face the wall portion 48 with a clearance left relative to the wall portion 48. Between the closing portion 52 and the wall portion 48, a blood introduction path 54 is disposed to guide the blood which has flowed from the blood inflow port 46*a*, into the accommodation space S.

The outer cylinder 40 is a cylindrical member arranged radially outside the core 38 with a clearance left therebetween. In the outer cylinder 40, a tubular blood outflow portion 56 is disposed. The blood outflow portion 56 forms a blood outflow port 56*a* through which the blood in the accommodation space S is allowed to flow out to an undepicted blood delivery line.

The first cover member 34 is fixed with an adhesive 58 on the one end portion of the housing main body 32 such that the heat exchange unit 28 and the gas exchange unit 30 are covered from the direction of the arrow X1. The first cover member 34 has a first cover main body 60, which faces a first inlet side end face 29*a* as one end face of the heat exchange unit 28 and a second inlet side end face 31*a* as one end face of the gas exchange unit 30. The first cover main body 60 includes a first partition section 66, which divides an internal space of the first cover member 34 into a first heat medium flow path 62*a* and a first gas flow path 64*a*. The first cover main body 60 is formed in an annular shape.

At a location on the first cover main body 60 where the first cover main body 60 faces the first inlet side end face 29*a* of the heat exchange unit 28, a tubular heat medium inflow portion 68 is disposed. The heat medium inflow portion 68 forms a heat medium inflow port 68*a* for allowing a heat medium (for example, water) to flow into the first heat medium flow path 62*a*. The heat medium inflow portion 68 extends radially outward from the first cover main body 60.

At a location on the first cover main body 60 where the first cover main body 60 faces the second inlet side end face 31*a* of the gas exchange unit 30, a tubular gas inflow portion 70 is disposed. The gas inflow portion 70 forms a gas inflow port 70*a* for allowing gas (oxygen gas and anesthetic gas) to flow into the first gas flow path 64*a*. The gas inflow port 70*a* communicates with the gas supply line 12 (see FIG. 1).

The first heat medium flow path 62*a* is a flow path for guiding the heat medium which has been guided from the heat medium inflow port 68*a*, into the heat exchange unit 28, and is located radially inside the first partition section 66. The first gas flow path 64*a* is a flow path for guiding the gas which has been guided from the gas inflow port 70*a*, into the gas exchange unit 30, and is located radially outside the first partition section 66.

Figure 3:
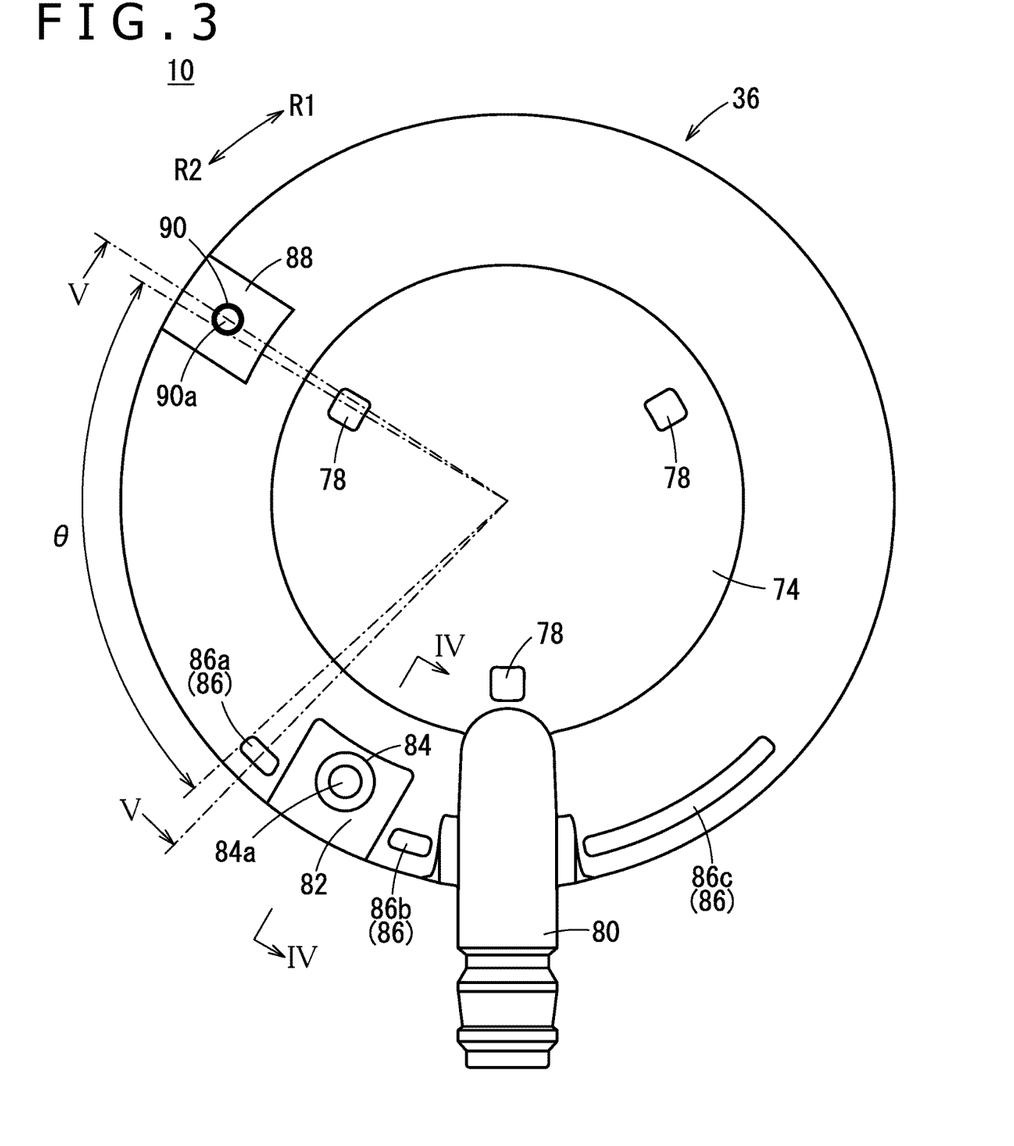
FIG. 3 is a side view of the oxygenator of FIG. 2 as viewed from a side of a second cover member.

The second cover member 36 is fixed with an adhesive 72 on the other end portion of the housing main body 32 such that the heat exchange unit 28 and the gas exchange unit 30 are covered from the direction of the arrow X2. As depicted in FIG. 3, the second cover member 36 has a second cover main body 74, a first recessed wall portion 82, and a second recessed wall portion 88.

In FIG. 2, the second cover main body 74 faces a first outlet side end face 29b as the other end surface of the heat exchange unit 28, and a second outlet side end face 31b as the other end face of the gas exchange unit 30. The second cover main body 74 includes a second partition section 76, which divides an internal space of the second cover member 36 into a second heat medium flow path 62b and a second gas flow path 64b.

In FIG. 3, the second cover main body 74 is formed in a circular shape. On an inner side of the second cover main body 74 adjacent the heat exchange unit 28, a plurality (three in the example of FIG. 3) of ventilation holes 78 are formed extending through the second cover main body 74. The ventilation holes 78 communicate a space inside the cylinder portion 50 and an external space (atmospheric air) with each other (see FIG. 5).

As depicted in FIG. 2, at a location on the second cover main body 74 where the second cover main body 74 faces the first outlet side end face 29b of the heat exchange unit 28, a tubular heat medium outflow portion 80 is disposed. The heat medium outflow portion 80 forms a heat medium outflow port 80a for allowing the heat medium to flow out from the second heat medium flow path 62b to an outside of the housing 26. The heat medium outflow portion 80 extends radially outward from the second cover main body 74.

Figure 4:
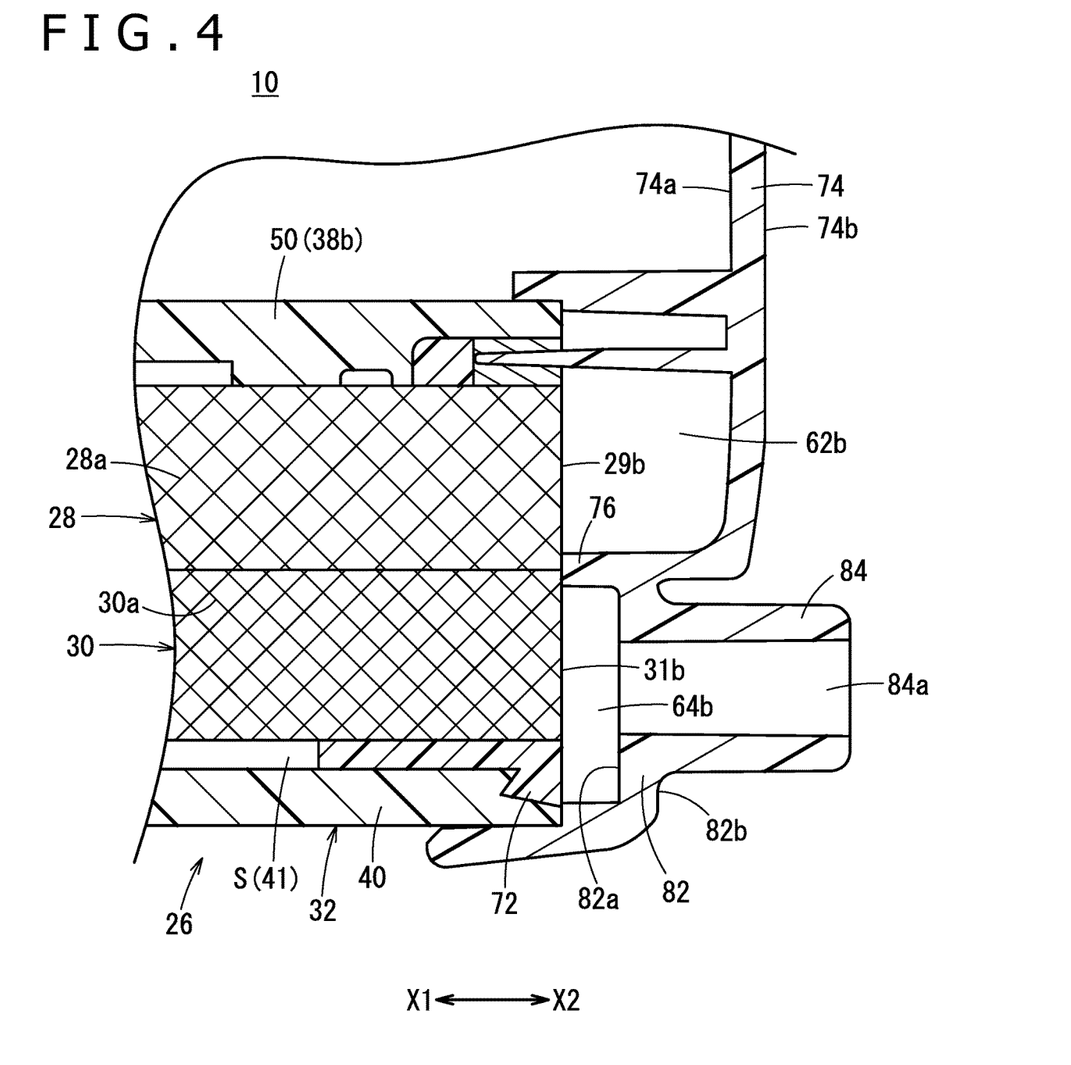
FIG. 4 is a cross-sectional view taken along line IV-IV of FIG. 3.

As depicted in FIG. 4, the first recessed wall portion 82 faces the second outlet side end face 31b of the gas exchange unit 30. The first recessed wall portion 82 is located in a vicinity of the heat medium outflow portion 80 (see FIG. 3). The first recessed wall portion 82 is recessed relative to the second cover main body 74 further in an axial direction (X1) toward a side of the gas exchange unit 30 than an inner surface 74a of the second cover main body 74.

In other words, a step is formed between the first recessed wall portion 82 and the second cover main body 74. An inner surface 82a of the first recessed wall portion 82 is located on a side closer by the step to the gas exchange unit 30 than the inner surface 74a of the second cover main body 74. An outer surface 82b of the first recessed wall portion 82 is located on a side closer by the step to the gas exchange unit 30 than an outer surface 74b of the second cover main body 74. The outer surface 82b of the first recessed wall portion 82 is located on a side closer to the gas exchange unit 30 than the inner surface 74a of the second cover main body 74.

On the first recessed wall portion 82, a tubular gas outflow portion 84 is disposed. The gas outflow portion 84 extends from the first recessed wall portion 82 toward a side opposite to the gas exchange unit 30 (in the direction of the arrow X2). Owing to this configuration, an extension length in the direction of the arrow X2 of the gas outflow portion 84 relative to the second cover main body 74 can be made shorter than a case in which the gas outflow portion 84 is disposed on the second cover main body 74. The gas outflow portion 84 forms a gas outflow port 84a for allowing the gas in the second gas flow path 64b to flow out to the outside of the housing 26. The gas outflow port 84a communicates with the gas discharge line 14 (see FIG. 1).

Figure 5:
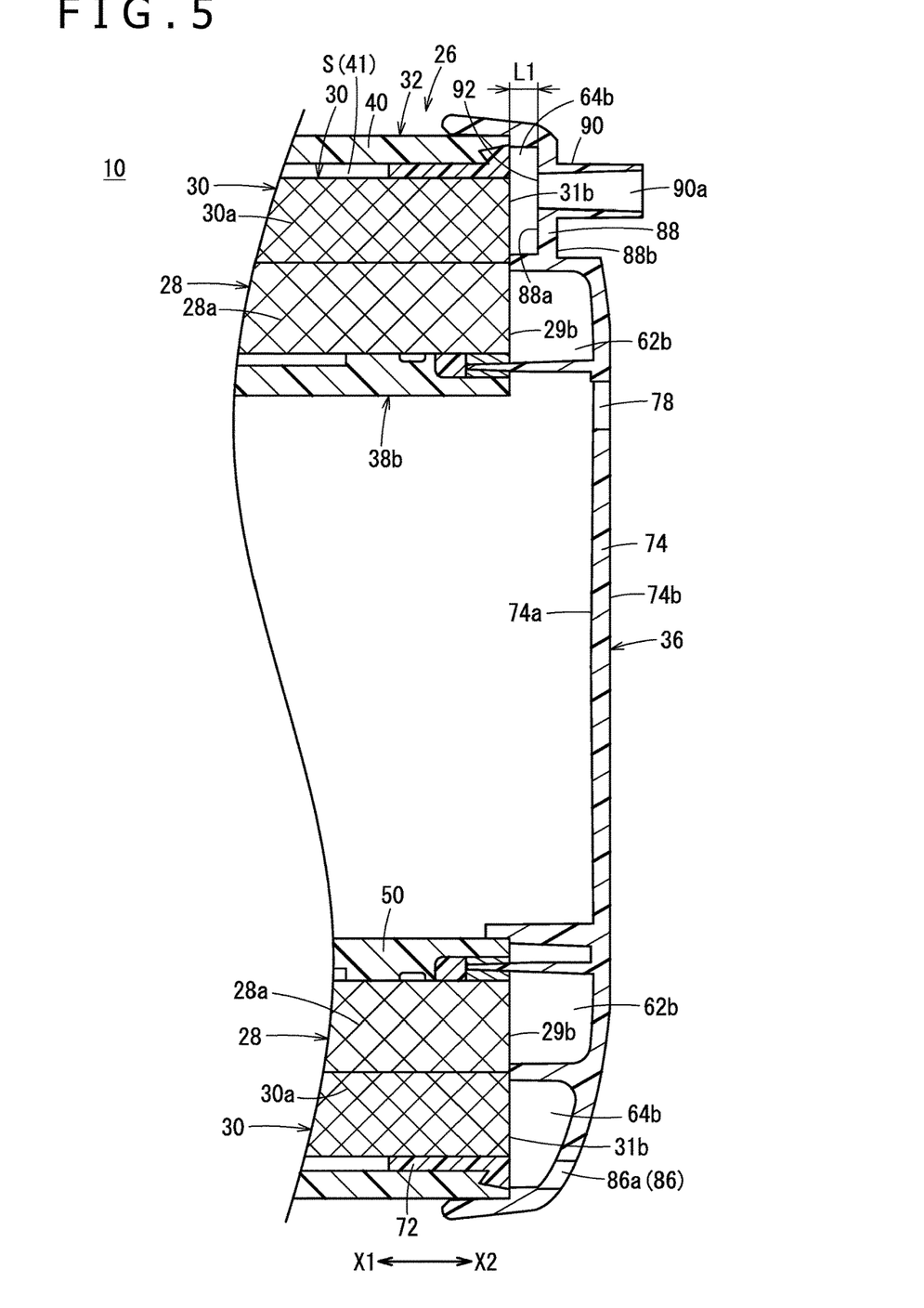
FIG. 5 is a cross-sectional view taken along line V-V of FIG. 3.

In FIGS. 3 and 5, at a location on the second cover main body 74 where the second cover main body 74 faces the second outlet side end face 31b of the gas exchange unit 30, a pressure control hole 86 is formed extending through the second cover main body 74 to control a pressure of the gas guided out from the gas exchange unit 30. In other words, the pressure control hole 86 functions as a pressure relief hole for suppressing the pressure in the second gas flow path 64b from rising excessively. The pressure control hole 86 is formed in an outer peripheral edge portion of the second cover main body 74.

As depicted in FIG. 3, the pressure control hole 86 may include a first hole 86a, a second hole 86b, and a third hole 86c. The first hole 86a is disposed adjacent the first recessed wall portion 82 in a peripheral direction (a direction of an arrow R1) of the second cover main body 74. The second hole 86b is disposed adjacent the first recessed wall portion 82 in a direction (a direction of an arrow R2) opposite to a side where the first hole 86a is located. In other words, the first hole 86a and the second hole 86b are arranged to flank the first recessed wall portion 82 in the peripheral direction of the second cover main body 74. The second hole 86b is located between the first recessed wall portion 82 and the heat medium outflow portion 80.

The third hole 86c is disposed adjacent the heat medium outflow portion 80 on a side opposite to a side where the second hole 86b is located (in a direction of the arrow R2). In other words, the second hole 86b and the third hole 86c are arranged to flank the heat medium outflow portion 80 in the peripheral direction of the second cover main body 74.

The first hole 86a, the second hole 86b, and the third hole 86c are each formed in an elongated (e.g., quasi-rectangular) shape. The third hole 86c extends longer than each of the first hole 86a and the second hole 86b in the peripheral direction of the second cover main body 74. However, the first hole 86a, the second hole 86b, and the third hole 86c may be formed using other shapes and sizes as appropriate.

The second recessed wall portion 88 is disposed spaced from the first hole 86a in a direction opposite to the side where the first recessed wall portion 82 is located (in the direction of the arrow R1). In FIG. 5, the second recessed wall portion 88 is recessed relative to the second cover main body 74 further toward the side of the gas exchange unit 30 than the inner surface 74a of the second cover main body 74.

In other words, a step is formed between the second recessed wall portion 88 and the second cover main body 74. An inner surface 88a of the second recessed wall portion 88 is located on a side closer by the step to the gas exchange unit 30 than the inner surface 74a of the second cover main body 74. An outer surface 88b of the second recessed wall portion 88 is located on a side closer by the step to the gas exchange unit 30 than the outer surface 74b of the second cover main body 74. The outer surface 88b of the second recessed wall portion 88 is located on a side closer to the gas exchange unit 30 than the inner surface 74a of the second cover main body 74.

The second recessed wall portion 88 includes a tubular port forming portion 90. The port forming portion 90 extends from the second recessed wall portion 88 toward a side opposite to the gas exchange unit 30 (in the direction of the arrow X2). The port forming portion 90 forms a sampling port 90a for collecting the gas guided out from the gas exchange unit 30. The gas collected from the sampling port 90a is provided for measurement of a gas concentration (e.g., an oxygen gas concentration or an anesthetic gas concentration).

In FIG. 3, the sampling port 90a is spaced by a predetermined angle θ or greater in the peripheral direction of the second cover main body 74 relative to the pressure control hole 86 (the first hole 86a). The predetermined angle θ is set, for example, at 60°. However, the predetermined angle θ can be changed as appropriate.

As depicted in FIG. 5, an inner opening portion 92 of the sampling port 90a, the inner opening portion 92 being located on a side of the gas exchange unit 30 (in the direction of the arrow X1), faces the second outlet side end face 31b of the gas exchange unit 30. A first distance L1 between the inner opening portion 92 and the second outlet side end face 31b is shorter than a second distance L2 (see FIG. 2) between the second outlet side end face 31b and the inner surface 74a of the second cover main body 74. Preferably, the first distance L1 may be set, for example, at 1 mm or greater and 5 mm or smaller, and the second distance L2 may be set at 7 mm or so. However, the first distance L1 and second distance L2 can be set as appropriate.

In FIG. 2, the heat exchange unit 28 is configured in a cylindrical shape comprised of a plurality of first hollow fiber membranes 28a. Each first hollow fiber membrane 28a is wound on an outer surface of the core 38 such that the first hollow fiber membrane 28a exists extending over the entire length of the heat exchange unit 28. Between the mutually adjacent first hollow fiber membranes 28a, gaps through which blood is flowable are formed. An opening portion (a heat medium inlet) on a side of one end of each first hollow fiber membrane 28a is located at the first inlet side end face 29a of the heat exchange unit 28 such that the opening portion communicates into the first heat medium flow path 62a. An opening portion (a heat medium outlet) on a side of the other end of each first hollow fiber membrane 28a is located at the first outlet side end face 29b of the heat exchange unit 28 so that the opening portion communicates into the second heat medium flow path 62b. Therefore, the heat medium flows into a lumen of each first hollow fiber membrane 28a.

The first hollow fiber membranes 28a are configured to allow no permeation of the heat medium and blood. Useful examples of the constituent material of the first hollow fiber membranes 28a include high molecular materials such as polypropylene, polyamide, polyethylene, polysulfone, polyacrylonitrile, polytetrafluoroethylene, and polymethylpentene, with polyamide being preferred. The inner diameter of the first hollow fiber membranes 28a is preferably set, for example, in a range of 50 to 700 μm. With such an inner diameter, the flow path resistance to the heat medium which flows through the lumens of the first hollow fiber membranes 28a can be made relatively small. The outer diameter of the hollow fiber membranes 28a is set preferably in a range of 100 to 1000 μm, and more preferably in a range of 120 to 800 μm. With such an outer diameter, the first hollow fiber membranes 28a can be efficiently provided with a large surface area.

The gas exchange unit 30 serves to supply oxygen gas and anesthetic gas to the blood flowing through the blood flow path 41, and also to eliminate carbon dioxide gas in the blood. The gas exchange unit 30 is disposed on an outer peripheral side of the heat exchange unit 28. Therefore, the gas exchange unit 30 and the heat exchange unit 28 are arranged such that they overlap each other in the radial direction. The gas exchange unit 30 has the same overall length as the heat exchange unit 28.

The gas exchange unit 30 is configured in a cylindrical shape comprised of a plurality of second hollow fiber membranes 30a. Each second hollow fiber membrane 30a is wound on an outer surface of the heat exchange unit 28 such that the second hollow fiber membrane 30a exists extending over the entire length of the gas exchange unit 30. Between the mutually adjacent second hollow fiber membranes 30a, gaps through which blood is flowable are formed. An opening portion (a gas inlet) on a side of one end of each second hollow fiber membrane 30a is located at the second inlet side end face 31a of the gas exchange unit 30 so that the opening portion communicates into the first gas flow path 64a. An opening portion (a gas outlet) on a side of the other end of each second hollow fiber membrane 30a is located at the second outlet side end face 31b of the gas exchange unit 30 such that the opening portion communicates into the second gas flow path 64b. Therefore, gas (carbon dioxide, anesthetic gas, or carbon dioxide gas) flows into a lumen of each second hollow fiber membrane 30a.

The second hollow fiber membranes 30a are configured to allow permeation of oxygen gas, anesthetic gas, or carbon dioxide gas, but not to allow permeation of blood. The constituent material and the inner diameter of the second hollow fiber membranes 30a can be set similar to those of the first hollow fiber membranes 28a.

A description will next be made about operation of the oxygenator 10 configured as described above.

Figure 6:
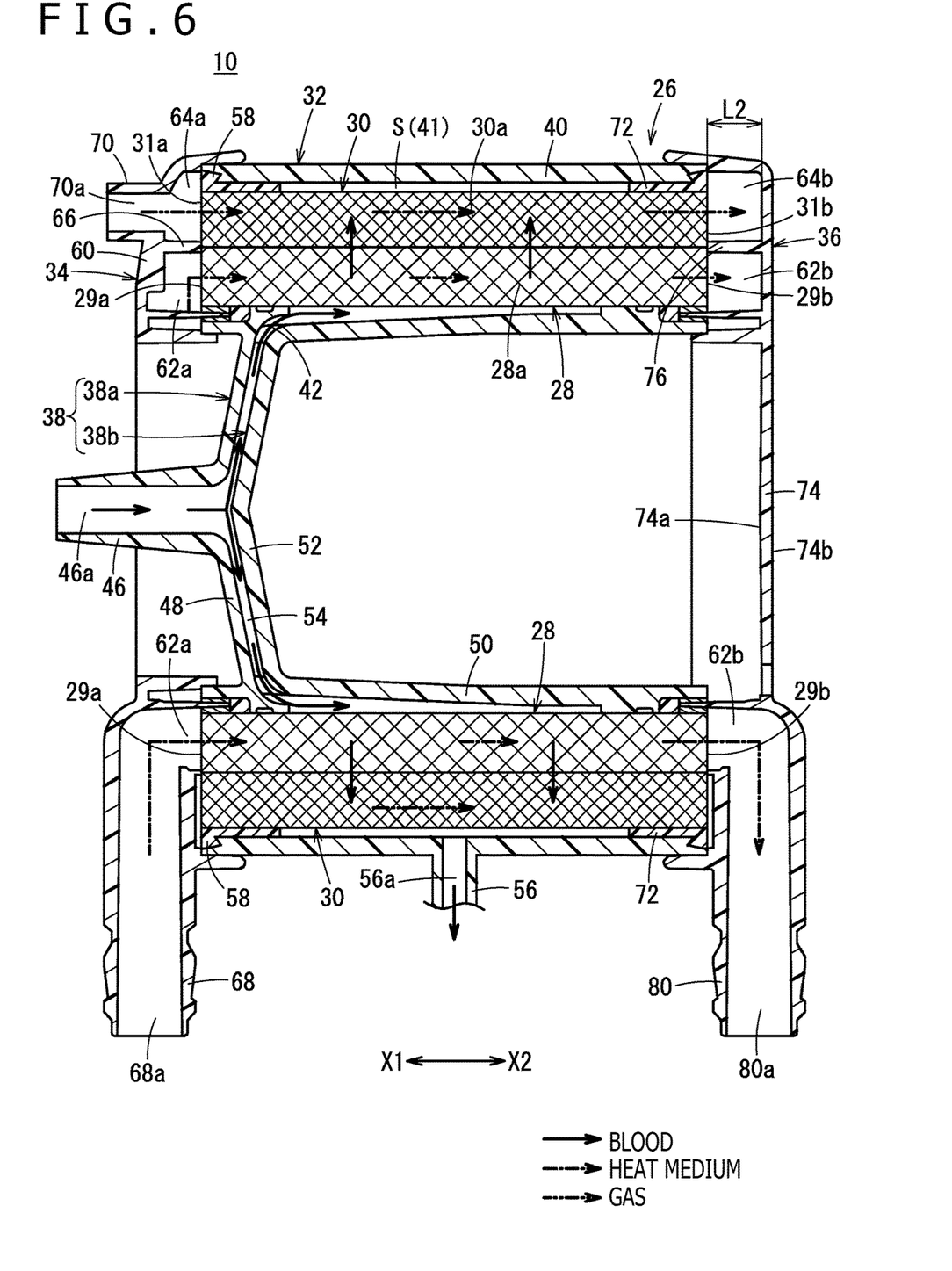
FIG. 6 is an operation explanatory diagram of the artificial lug of FIG. 2.

As illustrated in FIG. 6, the heat medium is supplied to the heat medium inflow port 68a of the oxygenator 10. The heat medium supplied to the heat medium inflow port 68a is guided from the first inlet side end face 29a of the heat exchange unit 28 into the lumen of each first hollow fiber membrane 28a via the first heat medium flow path 62a.

As illustrated in FIG. 1, oxygen gas is supplied from the oxygen blender 16 to the anesthetic vaporizer 20 via the gas supply line 12. At the anesthetic vaporizer 20, the anesthetic gas is mixed into the oxygen gas. As illustrated in FIG. 6, the oxygen gas and the anesthetic gas are then supplied to the gas inflow port 70a of the oxygenator 10. The oxygen gas and the anesthetic gas supplied to the gas inflow port 70a are guided from the second inlet side end face 31a of the gas exchange unit 30 into the lumen of each second hollow fiber membrane 30a via the first gas flow path 64a.

Blood guided from the patient via the blood removal line is supplied to the blood inflow port 46a of the oxygenator 10 under action of an undepicted centrifugal pump. The blood supplied to the blood inflow port 46a is guided to the blood flow path 41 (accommodation space S) via the blood introduction path 54. The blood guided to the blood flow path 41 flows, through the gaps between the adjacent first hollow fiber membranes 28 of the heat exchange unit 28, radially outward in the accommodation space S. As a consequence, heat exchange occurs between the heat medium flowing through the lumens of the first hollow fiber membranes 28a and the blood flowing outside the first hollow fiber membranes 28a.

The blood subjected to the heat exchange flows, through the gaps between the adjacent second hollow fiber membranes 30a of the gas exchange unit 30, radially outward in the accommodation space S. As a consequence, the oxygen gas and the anesthetic gas flowing through the lumens of the second hollow fiber membranes 30a permeate wall portions of the second hollow fiber membranes 30a and are supplied into the blood, and the carbon dioxide in the blood permeates the wall portions of the second hollow fiber membranes 30a and is discharged outside the second hollow fiber membranes 30a. Accordingly, the oxygen gas and the anesthetic gas are dissolved into the blood. The blood subjected to the gas exchange is guided from the blood outflow port 56a to the blood delivery line, and is returned to the patient.

The heat medium flowed through the heat exchange unit 28 is guided out from the first outlet side end face 29b of the heat exchange unit 28 to the second heat medium flow path 62b, and is drained outside the oxygenator 10 via the heat medium outflow port 80a. The gas (any remaining oxygen gas, any remaining anesthetic gas, or carbon dioxide gas) flowed through the gas exchange unit 30 is guided out from the second outlet side end face 31b of the gas exchange unit 30 to the second gas flow path 64b, and is discharged to the gas discharge line 14 (see FIG. 1) via the gas outflow port 84a. A portion of the remaining anesthetic gas guided to the gas discharge line 14 is guided to the anesthetic vaporizer 20 via the circulation line 22, and is reused. On the other hand, the anesthetic gas guided to the exhaust device 24 is discharged outside the operating room.

The oxygenator 10 according to this embodiment provides the following advantageous effects.

In the oxygenator 10, the second cover member 36 has the second cover main body 74 facing the second outlet side end face 31b of the gas exchange unit 30, and the second recessed wall portion 88 recessed relative to the second cover main body 74 further toward the side of the gas exchange unit 30 than the inner surface 74a of the second cover main body 74. In the second cover main body 74, the pressure control hole 86 is formed to control the pressure of the gas guided out from the gas exchange unit 30. In the second recessed wall portion 88, the sampling port 90a is disposed to collect the gas guided out from the gas exchange unit 30, and the inner opening portion 92 of the sampling port 90a, the inner opening portion 92 being located on the side of the gas exchange unit 30, faces the second outlet side end face 31b of the gas exchange unit 30.

According to the configuration as described above, the pressure control hole 86 is formed in the second cover main body 74, and the sampling port 90a is disposed in the second recessed wall portion 88 recessed closer toward the gas exchange unit 30 than the second cover main body 74. Owing to this configuration, the mixing of ambient air which might flow from the pressure control hole 86 into the housing 26 and then into the sampling port 90a can be suppressed compared with a case in which the sampling port 90a is disposed in the second cover main body 74 without such a step. In addition, the inner opening portion 92 of the sampling port 90a faces the second outlet side end face 31b of the gas exchange unit 30, so that the gas guided out from the second outlet side end face 31b of the gas exchange unit 30 can be efficiently guided into the sampling port 90a.

The second cover main body 74 is formed in the circular shape, and the sampling port 90a is spaced by 60° or greater in the peripheral direction of the second cover main body 74 relative to the pressure control hole 86.

According to such configurations, the mixing of ambient air which has flowed through the pressure control hole 86 into the sampling port 90a can be suppressed further.

The pressure control hole 86 is located in a vicinity of the gas outflow port 84a.

According to such a configuration, ambient air flowed from the pressure control hole 86 into the second gas flow path 64b can be efficiently discharged outside from the gas outflow port 84a.

The pressure control hole 86 includes the plurality of holes (the first hole 86a, the second hole 86b, and the third hole 86c).

According to such a configuration, the pressure of the gas guided out from the gas exchange unit 30 can be effectively controlled.

The first distance L1 between the inner opening portion 92 of the sampling port 90a and the second outlet side end face 31b of the gas exchange unit 30 is set at 1 mm or greater and 5 mm or smaller.

According to such a configuration, the discharge gas guided out from the gas exchange unit 30 can be efficiently guided to the sampling port 90a.

The present invention should not be restricted to the above-mentioned embodiment, and various modifications can be made within a scope not departing from the spirit of the present invention.

The foregoing embodiment can be summarized as follows.

The above-described embodiment discloses the oxygenator (10) including the gas exchange unit (30) having hollow fiber membranes (30a) that allow blood to undergo gas exchange, and the housing (26) provided with the gas inflow port (70a) and the gas outflow port (84a), the housing having the housing main body (32) with the gas exchange unit accommodated therein, the first cover member (34) disposed on the one end portion of the housing main body such that the gas exchange unit is covered at the inlet side end face (31a) thereof where the gas inlets of the hollow fiber membranes are located, and the second cover member (36) disposed on the other end portion of the housing main body such that the gas exchange unit is covered at the outlet side end face (31b) thereof where the gas outlets of the hollow fiber membranes are located. The second cover member has the cover main body (74) facing the outlet side end face of the gas exchange unit, and the recessed wall portion (88) recessed relative to the cover main body further toward a side of the gas exchange unit than an inner surface (74a) of the cover main body. The pressure control hole (86) is formed through the cover main body to control the pressure of gas guided out from the gas exchange unit. The sampling port (90a) is disposed in the recessed wall portion to collect the gas guided out from the gas exchange unit. The sampling port faces, at the inner opening portion (92) thereof on the side of the gas exchange unit, the outlet side end face of the gas exchange unit.

In the oxygenator described above, the cover main body may be formed in the circular shape, and the sampling port may be spaced by 60° or greater in the peripheral direction of the cover main body relative to the pressure control hole.

In the oxygenators described above, the pressure control hole may be located in close proximity to the gas outflow port.

In the oxygenators described above, the pressure control hole may include the plurality of holes (86a to 86c).

In the oxygenators described above, the distance (L1) between the inner opening portion of the sampling port and the outlet side end face of the gas exchange unit may be set in a range from 1 mm to 5 mm.

The invention claimed is:

1. An oxygenator comprising:
   a gas exchange unit having hollow fiber membranes extending between first and second longitudinal ends and being configured to allow blood to undergo gas exchange, wherein the first longitudinal end comprises an inlet side end face thereof where gas inlets of the hollow fiber membranes are located, and wherein the second longitudinal end comprises an outlet side end face thereof where gas outlets of the hollow fiber membranes are located; and
   a housing provided with a gas inflow port and a gas outflow port, wherein the housing is comprised of:
   a housing main body with the gas exchange unit accommodated therein;
   a first cover member disposed on one end portion of the housing main body enclosing the first longitudinal end of the gas exchange unit; and
   a second cover member disposed on another end portion of the housing main body enclosing the second longitudinal end of the gas exchange unit;

wherein the housing main body further accommodates a core with a cylinder portion at a central part of the oxygenator;

wherein the second cover member includes a cover main body facing the outlet side end face of the gas exchange unit, a recessed wall portion which is recessed relative to the cover main body to be closer to the outlet side end face of the gas exchange unit than an inner surface of the cover main body facing the core, a pressure control hole formed through the cover main body spaced away from the recessed wall portion to control a pressure of gas guided out from the gas exchange unit, and a sampling port disposed in the recessed wall portion to collect a respective portion of the gas guided out from the gas exchange unit, wherein the sampling port faces, at an inner opening portion thereof, the outlet side end face of the gas exchange unit.

2. The oxygenator according to claim 1, wherein:

the cover main body is formed in a circular shape; and the sampling port is spaced by 60° or greater in a peripheral direction of the cover main body relative to the pressure control hole.

3. The oxygenator according to claim 1, wherein the pressure control hole is located proximate to the gas outflow port.

4. The oxygenator according to claim 1, wherein the pressure control hole includes a plurality of spaced holes disposed proximate to the gas outflow port.

5. The oxygenator according to claim 1, wherein a distance between the inner opening portion of the sampling port and a closest portion of the outlet side end face of the gas exchange unit is set in a range from 1 mm to 5 mm.

6. An oxygenator for treating an extracorporeal blood flow, comprising:

a cylindrical housing with a first cover member at a first end defining a gas inlet and a second cover member at a second end defining a gas outlet and a sampling port; and a gas exchange unit comprised of cylindrically-wound hollow fiber membranes each extending from an annular inlet side end face proximate the first cover member to an annular outlet side end face proximate the second cover member;

wherein the cylindrical housing accommodates a core with a cylinder portion at a central part of the oxygenator;

wherein the second cover member has a main wall portion facing the core and spaced from the outlet side end face of the gas exchange unit by a first distance and a recessed wall portion spaced from the outlet side end face of the gas exchange unit by a second distance which is less than the first distance;

wherein the second cover member includes a pressure control hole facing the annular outlet side end face and configured to provide pressure relief within the housing;

wherein the sampling port is disposed on the recessed wall portion so that an inner end of the sampling port faces the outlet side end face and is spaced away from the pressure control hole, whereby a gas flowing from the gas exchange unit flows to the sampling port more efficiently than an ambient air flowing through the pressure control hole.

7. The oxygenator of claim 6 wherein the sampling port is spaced by 60° or greater in a peripheral direction of the second cover member relative to the pressure control hole.

8. The oxygenator of claim 6 wherein the pressure control hole is located proximate to the gas outlet.

9. The oxygenator of claim 6 wherein the first distance is set in a range from 1 mm to 5 mm.

* * * * *